(12) United States Patent
Sugimoto et al.

(10) Patent No.: US 7,725,013 B2
(45) Date of Patent: May 25, 2010

(54) ELECTRONIC ENDOSCOPE WITH BRIGHTNESS ADJUSTMENT FUNCTION

(75) Inventors: Hideo Sugimoto, Tokyo (JP); Kohei Iketani, Saitama (JP)

(73) Assignee: Hoya Corporation, Tokyo (JP)

( * ) Notice: Subject to any disclaimer, the term of this patent is extended or adjusted under 35 U.S.C. 154(b) by 396 days.

(21) Appl. No.: 11/616,100

(22) Filed: Dec. 26, 2006

(65) Prior Publication Data

US 2007/0147810 A1 Jun. 28, 2007

(30) Foreign Application Priority Data

Dec. 26, 2005 (JP) ............................ P2005-372531

(51) Int. Cl.
*A61B 1/04* (2006.01)
(52) U.S. Cl. ......................................... 396/17; 396/493
(58) Field of Classification Search ................... 396/17, 396/45, 493, 495; 348/230.1, 221.1, 367 348/368; 352/208, 219, 220
See application file for complete search history.

(56) References Cited

U.S. PATENT DOCUMENTS

| 2,513,702 | A | * | 7/1950 | Andrews | ..................... 352/220 |
| 4,884,134 | A | * | 11/1989 | Tsuji et al. | ..................... 348/73 |
| 6,542,194 | B1 | * | 4/2003 | Juen | ........................... 348/367 |
| 6,582,363 | B2 | | 6/2003 | Adachi et al. | |
| 6,635,011 | B1 | * | 10/2003 | Ozawa et al. | ............... 600/178 |
| 6,663,561 | B2 | | 12/2003 | Sugimoto et al. | |
| 6,677,992 | B1 | * | 1/2004 | Matsumoto et al. | ...... 348/229.1 |
| 6,902,527 | B1 | * | 6/2005 | Doguchi et al. | ............. 600/109 |
| 7,625,336 | B2 | * | 12/2009 | Fukuyama et al. | ........... 600/118 |
| 2002/0042556 | A1 | * | 4/2002 | Sugimoto et al. | ............ 600/178 |
| 2003/0164893 | A1 | * | 9/2003 | Mayhew | ..................... 348/368 |
| 2004/0092792 | A1 | * | 5/2004 | Kobayashi | .................. 600/101 |
| 2005/0010083 | A1 | | 1/2005 | Iriyama | |
| 2005/0220447 | A1 | * | 10/2005 | Ito | ............................... 396/17 |

(Continued)

FOREIGN PATENT DOCUMENTS

JP 2002-65602 3/2002

(Continued)

OTHER PUBLICATIONS

English language Abstract of JP 2003-93336.

(Continued)

*Primary Examiner*—W. B. Perkey
*Assistant Examiner*—Dennis Hancock
(74) *Attorney, Agent, or Firm*—Greenblum & Bernstein P.L.C.

(57) ABSTRACT

An electronic endoscope has a video-scope with an image sensor, a light source that emits illuminating-light to illuminate an object, an image sensor driver, a luminance detector, one rotary shutter, and a brightness adjuster. The luminance detector detects a luminance of an object image on the basis of image-pixel signals read from the image sensor. The rotary shutter has a light-transmitting portion that transmits the illuminating light, and a shield portion that blocks the illuminating light. The brightness adjuster controls the rotary shutter to adjust an irradiation-interval of the illuminating-light in accordance with a charge accumulation interval. The brightness adjuster shifts a rotation-phase of the rotary shutter by changing a rotation-speed on the basis of the detected luminance, so as to maintain a brightness of the object image at a proper brightness.

20 Claims, 6 Drawing Sheets

U.S. PATENT DOCUMENTS

| | | | |
|---|---|---|---|
| 2006/0020169 A1* | 1/2006 | Sugimoto | 600/180 |
| 2006/0082845 A1* | 4/2006 | Watanabe | 358/509 |
| 2007/0010712 A1 | 1/2007 | Negishi | |
| 2007/0100205 A1* | 5/2007 | Iriyama | 600/118 |

FOREIGN PATENT DOCUMENTS

| | | |
|---|---|---|
| JP | 2002-112949 | 4/2002 |
| JP | 2002-119464 | 4/2002 |
| JP | 2002-136468 | 5/2002 |
| JP | 3370871 | 11/2002 |
| JP | 3403596 | 2/2003 |
| JP | 2003-93336 | 4/2003 |

OTHER PUBLICATIONS

English language Abstract of JP 2002-136468.
English language Abstract of JP 2002-119464.
English language Abstract of JP 2002-65602.
English language Abstract of JP 2002-112949.

* cited by examiner

ELECTRONIC ENDOSCOPE WITH BRIGHTNESS ADJUSTMENT FUNCTION

BACKGROUND OF THE INVENTION

1. Field of the Invention

The present invention relates to electronic endoscope that observes an observed portion, such as a body cavity. In particular, it relates to a brightness adjustment process using a rotary shutter 2. Description of the Related Art In an endoscope with a brightness adjustment function, an amount of illuminating-light radiated on an observed object is adjusted by using a stop, or an electronic shutter function is adjusted. In an electronic endoscope with a video-scope, a luminance of the object image is detected on the basis of image-pixel signals, which are successively read from a CCD provided in the video-scope. Then, an opening-degree of a stop or an electronic shutter speed (charge-accumulation interval) is adjusted such that the displayed object image is maintained at a proper brightness In the case of an electronic endoscope with a rotary shutter mechanism, two rotary shutters opposite each other are arranged between a lamp and a light-guide or fiber-optic bundle; and are driven so as to rotate at a constant speed in synchronization with each other. Each rotary shutter has a light-transmitting portion that transmits illuminating-light, and a shield portion blocking the illuminating light. To adjust the brightness of the observed image, an overlapped area of the two light-transmitting portions, which allows illuminating-light to progress toward the incident surface of the light-guide, is changed by shifting a relative position of one rotary shutter relative to that of the other rotary shutter before performing the brightness adjustment process.

SUMMARY OF THE INVENTION

An object of the present invention is to provide an electronic endoscope that is capable of adjusting a brightness of an object image by using a simple mechanism with one rotary shutter.

An electronic endoscope according to the present invention has a video-scope with an image sensor, alight source that emits illuminating-light for illuminating an object, and an image sensor driver that outputs pulse signals for transferring charges accumulated in the image sensor in each field/frame interval on the basis of a charge accumulation interval. The image sensor driver further outputs a pulse signals for discarding accumulated charges at regular intervals. The electronic endoscope further has a luminance detector, one rotary shutter, and a brightness adjuster. The luminance detector detects a luminance of an object image on the basis of image-pixel signals read from the image sensor. The rotary shutter has a light-transmitting portions that transmits the illuminating-light and a shield portion that blocks the illuminating light. The rotary shutter rotates while the light-transmitting portion and the shield portion alternately cross a light-path of the illuminating-light. The brightness adjuster controls the rotary shutter so as to adjust an irradiation-interval of the illuminating-light to the charge accumulation interval. While the brightness adjustment process is performed, the brightness adjuster shifts a rotation-phase of the rotary shutter by changing a rotation-speed on the basis of the detected luminance, so as to maintain a brightness of the object image at a proper brightness.

For example, to prevent a leak of illuminating light, the image sensor driver adjusts the charge accumulation interval to the irradiation interval in one field/frame interval in accordance with the shifted rotation-phase.

To prevent excessive electric power consumption, for example, a light source controller is provided. The light source controller is capable of selectively setting intensity level of illuminating light to one of a normal level required for illuminating an object and a low level adjacent to zero level. Then, the light source controller sets the normal level to the irradiation interval, and sets the low level to the other interval.

An apparatus for adjusting a brightness of an object image in an electronic endoscope according to another aspect of the present invention has a luminance detector that detects a luminance level of an object image on the basis of image-pixel signals that are read from an image sensor of a video-scope successively, and one rotary shutter comprising a light-transmitting portion and a shield portion. The rotary shutter rotates while the light-transmitting portion and the shield portion cross a light-path of the illuminating light alternately. The apparatus further has a brightness adjuster that controls the rotary shutter to adjust an irradiation interval of the illuminating light to a charge accumulation interval of the image sensor. The brightness adjuster changes an overlapping interval of the irradiation interval and the charge accumulation interval by shifting a rotation-phase of the rotary shutter on the basis or the detected luminance level, so as to maintain a brightness of the object image at a proper brightness.

A method for adjusting a brightness of an object image in an electronic endoscope according to another aspect of the present invention has i) detecting a luminance level of an object image on the basis of image-pixel signals that are read from an image sensor of a video-scope successively; ii) rotating one rotary shutter that comprises a light-transmitting portion and a shield portion, such that the rotary shutter rotates while the light-transmitting portion and the shield portion cross a light-path of the illuminating-light alternately; and iii) controlling the rotary shutter to adjust an irradiation interval of the illuminating light in accordance with a charge accumulation interval of the image sensor. Then, the method changes an overlapping interval of the irradiation interval and the charge accumulation interval by shifting a rotation-phase of the rotary shutter on the basis of the detected luminance level, so as to maintain a brightness of the object image at a proper brightness.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiments of the present invention are described with reference to the attached drawings.

Figure 1:
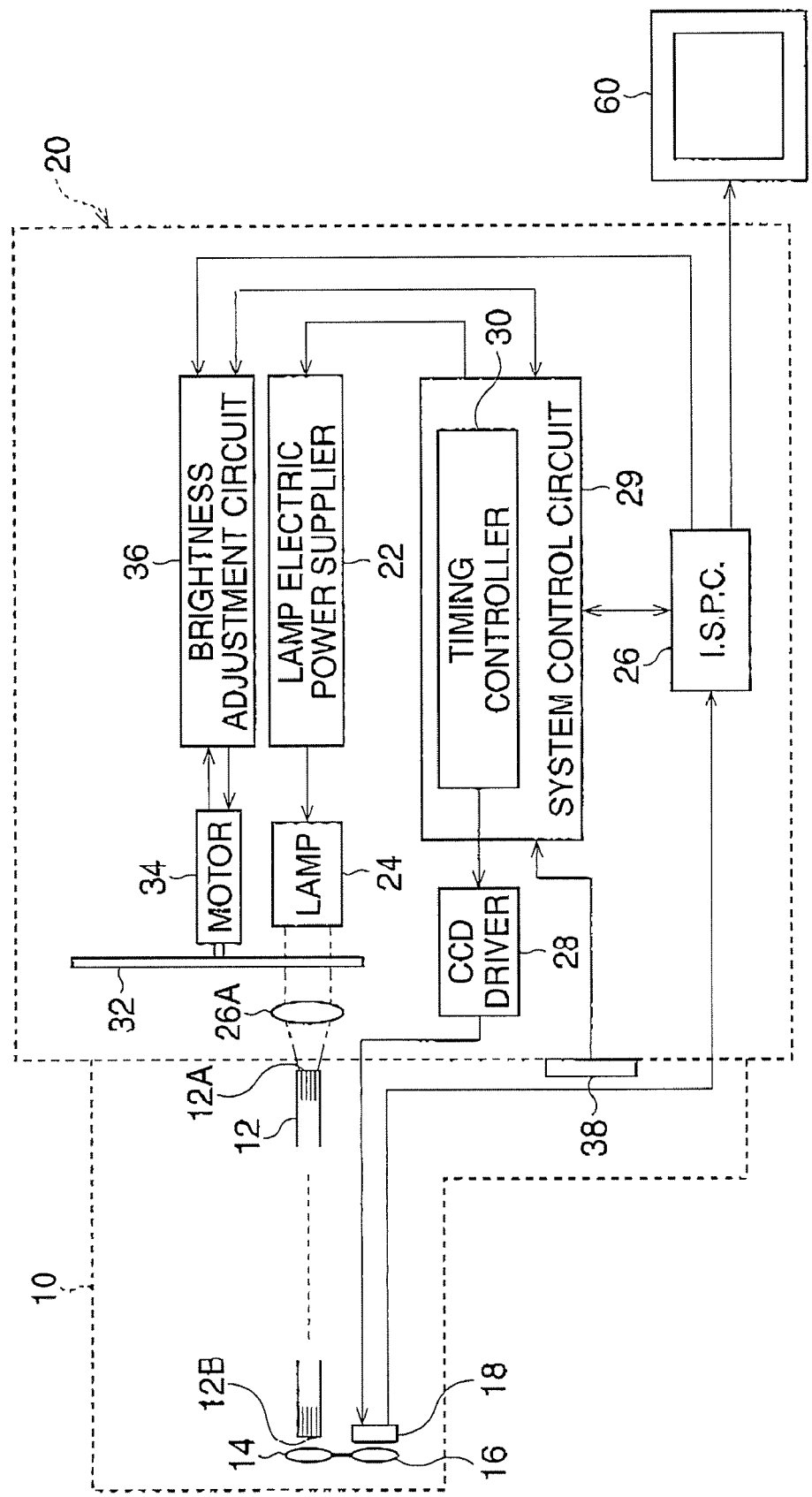
FIG. 1 is a block diagram of an electronic endoscope according to a first embodiment.

FIG. 1 is a block diagram of an electronic endoscope according to a first embodiment.

The electronic endoscope has a video-scope 10 with a CCD 18, and a video-processor 20. The video-scope 10 is removably connected to the video-processor 20; and a monitor 60 is connected to the video-processor 20.

When a lamp switch button (not shown) is turned ON, a lamp electric power supplier 22 supplies electric power to a lamp 24 so that the lamp 24 emits illuminating light. The illuminating light emitted from the lamp 24 enters the incident surface 12A of a light-guide 12 via a rotary shutter 32 and a collecting lens 26A. The light-guide 12, constructed of a fiber-optic bundle, directs the illuminating light to a distal end of the video-scope 10. The light exits from the distal end surface 12B of the light-guide 12, and is irradiated on an object via a diffusion lens 14.

Light, reflected off the object, reaches the inter-line transfer type CCD 18 via an objective lens 16, so that an object image is formed on the photo-sensitive area of the CCD 18. A color filter (not shown), checkered by four color elements of Yellow (Y), Magenta (M), Cyan (C), and Green (G), is arranged on the photo-receiving urea ouch that the four color elements are opposite to pixels arranged in the photo-sensitive area. Based on the light passing through each color element, analog image-pixel signals are generated by the photoelectric transformation effect. As for the imaging process, a color difference line sequential method using an on-chip color filter is herein applied.

The generated image-pixel signals are read from the CCD 18 to an image signal processing circuit 26 at regular time intervals, in accordance with clock pulse signals output from a CCD driver 28. The NTSC (or PAL) standard is herein applied as the TV standard; therefore, the image-pixel signals are read from the CCD 18 at a 1/60 (or 1/50) second intervals.

In the image signal processing circuit 26, various processes, such as a gamma correction process, a white balance process, and so on, are carried out, so that video signals are generated. The generated video signals are output to the monitor 60 so that an observed image is displayed on the monitor 60. Also, luminance signals generated in the image signal processing circuit 26 are output to a brightness adjustment circuit 36 at one-field intervals, A system control circuit 29, which includes a CPU, a RAM, and a ROM (not shorn), controls an operation of the video-processor 20 by outputting control signals to circuits. Further, the system control circuit 29 controls the lamp electric power supplier 22 so that the intensity of illuminating-light is adjusted. The timing controller 30 outputs clock pulse signals to each circuit to adjust the timing of signal processes. A reference luminance level button 38 provided on a front panel of the video-processor 20 is operated to set a standard brightness of the displayed object image.

The rotary shutter 32 rotates by a stepping motor 34 with an encoder (herein not shown), which is coaxially attached to the rotary shutter 32. The stepping motor 34 rotates in accordance with driving pulse signals fed from the brightness adjustment circuit 36. The timing controller 30 outputs clock pulse signals to adjust or synchronize the rotation of the rotary shutter 32 with the reading of the image-pixel signals from the CCD 18. Then, to maintain the brightness of an object image displayed on the monitor 60 at a proper brightness, the brightness adjustment circuit 36, constructed of a DSP (Digital Signal Processor), controls a rotation of the stepping motor 34; i.e., of the rotary shutter 32. Concretely speaking, the brightness adjustment circuit 36 controls a rotation-phase of the rotary shutter 32 in accordance with a luminance difference between the detected luminance level fed from the image signal processing circuit 26 and the reference luminance level set by the reference luminance level button 38, as described later.

Figure 2:
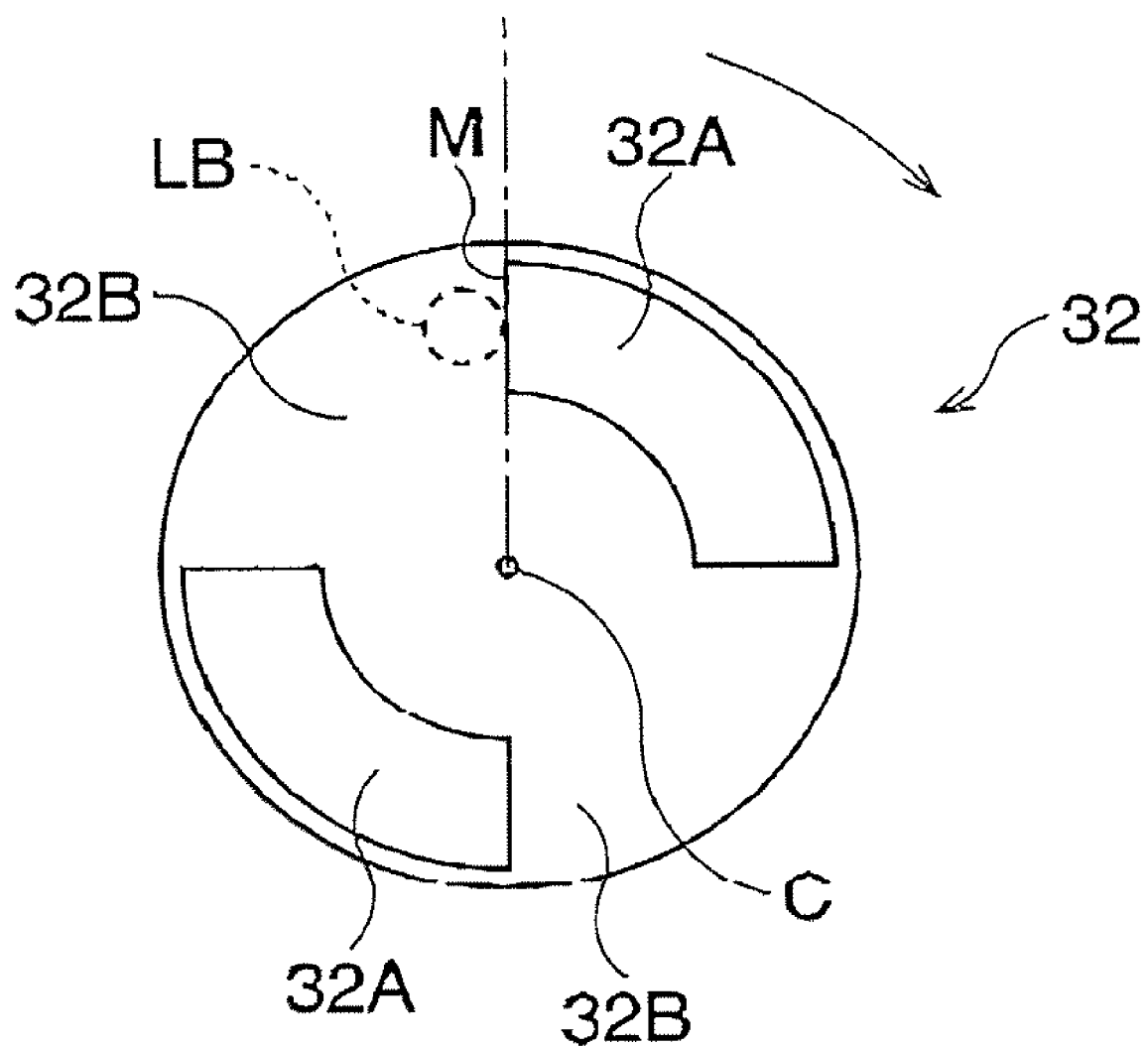
FIG. 2 is a schematic plan view of the rotary shutter.

FIG. 2 is a schematic plan view of the rotary shutter 32.

The disk-shaped rotary shutter 32 has a pair of arc-shaped aperture portions 32A opposite each other, which each extend circumferentially by a quarter-circle. The aperture portions 32A transmit the light emitted from the lamp 24 toward the incident surface 12A of the light-guide 12, whereas the other portion; namely, a shield portion 32B, blocks the light.

The rotary shutter 32 is positioned such that the light-path LB of the illuminating-light faces the peripheral portion of the rotary shutter 32; thus, the pair of aperture portions 32A and the shield portion 32B cross the light-path LB alternately while the rotary shutter 32 rotates. The rotary shutter 32 rotates by a half-rotation in a one-field interval; namely, the rotary shutter 32 rotates by a half-rotation at 1/60 (or 1/50) second intervals.

Figure 3:
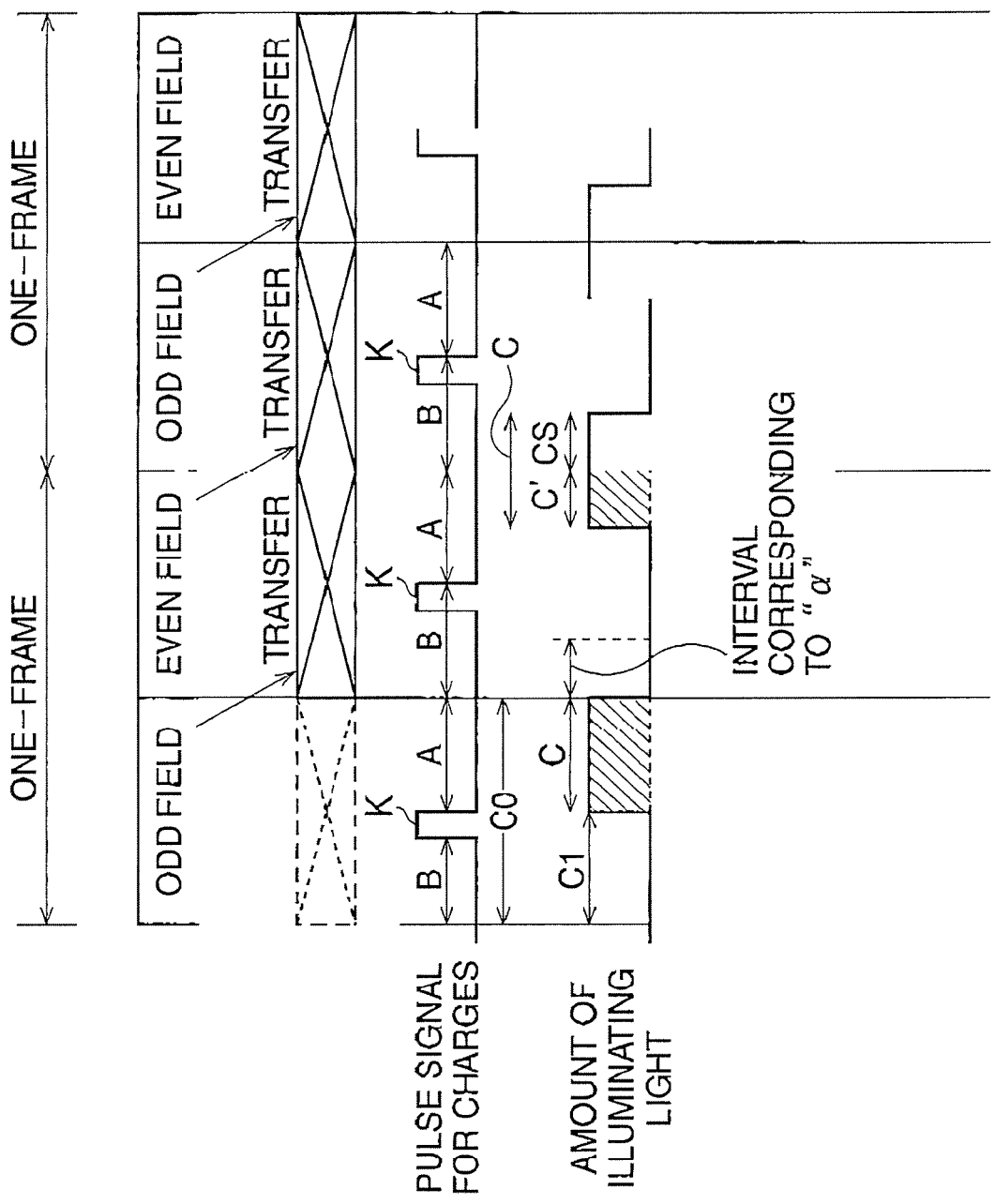
FIG. 3 it a view showing a timing chart of the brightness adjustment process.

FIG. 3 is a view showing timing chart of the brightness adjustment process.

The one-field interval, represented by "C0" is constructed of an irradiation interval "C" in which one aperture portion 32A crosses the light-path LB, and another interval or a blocking interval "C1" in which the shield portion 32B crosses the light-path LB. On the other hand, the CCD driver 28 outputs pulse signals for transferring accumulated charges to the image signal processing circuit 26 in each field interval. Also, the CCD driver 28 outputs a clock pulse signal "K" for sweeping accumulated charges to a substrate (not shown) of the CCD 18 at regular intervals, so that accumulated charges in an interval "B" before the output of the pulse signal "K" are discarded, whereas accumulated charges in an interval (hereinafter, called a "charge accumulation interval") "A" after the output of the pulse signal "K" are transferred or read from the CCD 18 at the next field interval. Herein, the output-timing of the clock pulse signal "K", defining the charge accumulated interval "A", is based on the illuminating interval "C". When the charge accumulation interval "A" coincides with the irradiation interval "C", all of the illuminating-light during the irradiation interval "A" is utilized for generating charges.

As described above, based on the luminance difference between the detected luminance level of one field-worth of image signal and the predetermined reference luminance level, the brightness adjustment circuit 36 determines whether the brightness of the object image is appropriate. If a substantial luminance discrepancy occurs, in other words, if the luminance difference exceeds a predetermined tolerance difference, the rotation-phase of the rotary shutter 32 is shifted. The rotation-phase is represented by a rotation-angle, which is based on the relative rotation-position of the initial portion of the shield portion 32B (designated by "M" in FIG. 2) in a one-field interval. The rotation-angle at the instant that the initial portion or the shield portion 32B starts passing through the light-path LB at the start timing of a one-field interval, is herein set to a standard angle (=0 degrees). Then, the rotation-phase is defined as an angle of difference from the standard angle at the start of the one-field interval.

While the luminance difference is within a tolerance level, the rotary shutter 32 rotates at a constant speed in a state in which the rotation-phase is maintained. When the detected luminance level exceeds the reference luminance level and the brightness of the object image exceeds the proper brightness, the rotation-phase is shifted by changing the rotation-speed of the rotary shutter 32 so as to decrease the amount of illuminating-light. The rotation-speed of the rotary shutter 32 is hereby decreased to shift a rotation-phase by an amount or angle corresponding to the luminance difference. The rotation-speed of the rotary shutter 32 decreases by lowering a period of pulse signals output from the brightness adjustment circuit 36 to the stepping motor 34.

In FIG. 3, the rotation-phase is shifted by an angle "α", and the irradiation interval "C" is shifted relative to the charge accumulation interval "A" by the interval "CS". The part of the irradiation interval "C" is herein represented by a reference numeral "C'", which is included or accommodated in the charge accumulation interval "A". The shifted interval "CS" belongs to the interval "B" before the output of the pulse signal "K"; therefore, charges accumulated in the interval "CS" are erased or discarded, and only charges accumulated in the interval "C'" are used for generating image signals. Consequently, the amount of illuminating-light decreases, and the brightness of the object image changes to a proper brightness. While a substantial difference in luminance does not substantially occur, the rotary shutter 34 rotates at regular intervals in a state in which the shifted rotation-phase is maintained.

On the other hand, when the brightness of the object image decreases, the rotation-speed of the rotary shutter 34 is increased by increasing the period of pulse signals output to the motor 34A Consequently, the rotation-phase is shifted by a give on angle corresponding to the luminance difference, such that the overlapped interval of the irradiation interval "C" and the charge accumulation interval "A" becomes longer; i.e., the amount of illuminating light increases on the basis of the luminance difference.

Figure 4:
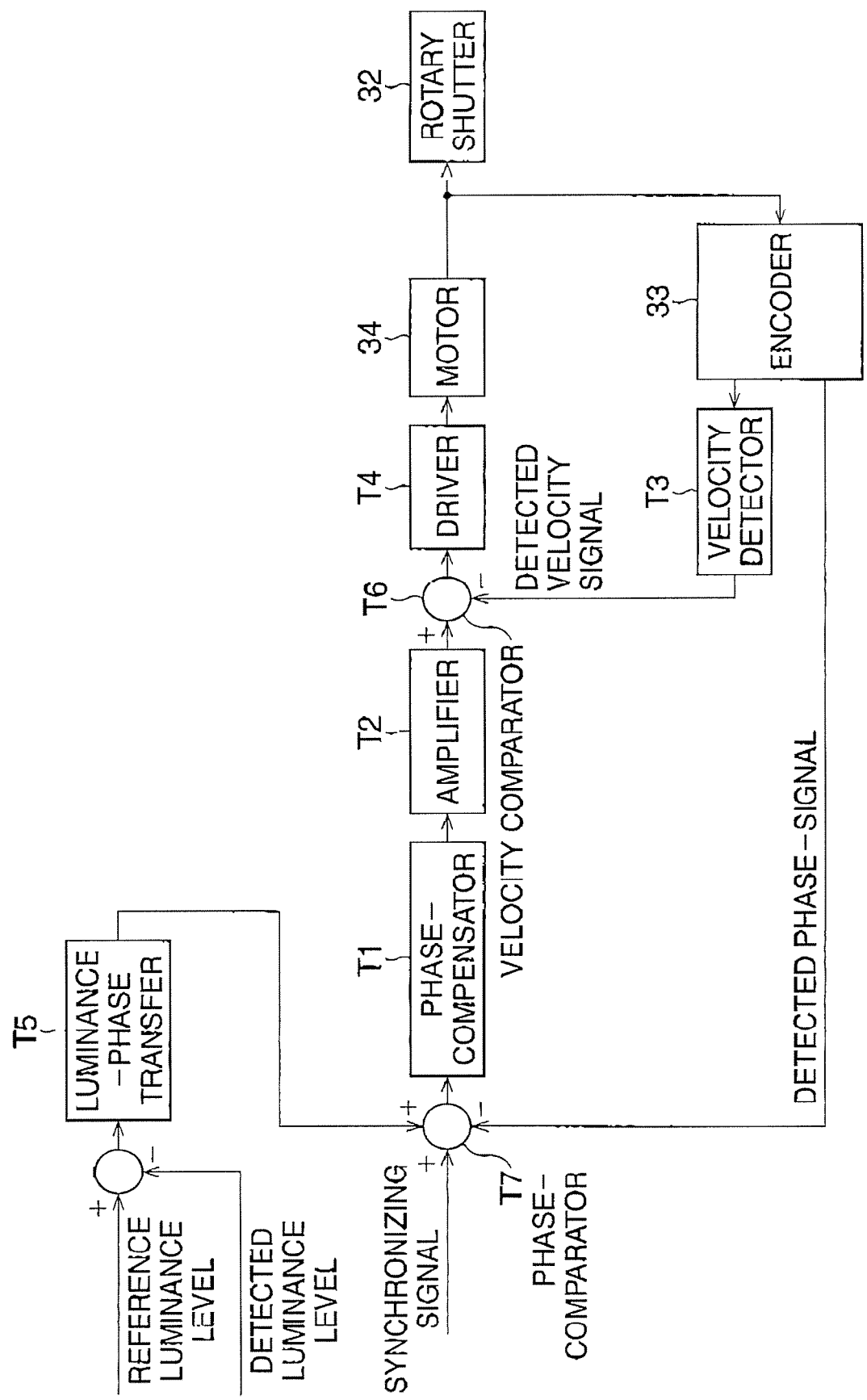
FIG. 4 is a control block diagram of the brightness adjustment process.

FIG. 4 is a control block diagram of the brightness adjustment process.

The control system according to the brightness adjustment process has a phase-compensator T1, an amplifier T2, a velocity detector T3, and a driver T4. In a luminance-phase transfer T5, the predetermined reference luminance level signal is added to the detected luminance level signal, and the difference is transferred to a rotation-phase signal that represents an amount or rotation-angle or rotation-phase to be shifted.

The rotation-phase signal is added to a detected rotation-phase signal, which is detected by the encoder 33, in a phase-comparator T7, and is input to the phase-compensator T1 with a synchronizing signal fed from the timing controller 30. In the phase-compensator T1, based on the amount of rotation-phase to be shifted, a velocity signal for increasing or decreasing the rotation-speed of the rotary shutter 32 is output to the amplifier T2. The velocity signal amplified in the amplifier T2 is added to a detected velocity signal, fed from the velocity detector T3, in a velocity comparator T6. Then, a control signal is output from the velocity comparator T6 to the driver T4. In the driver T4, based on the determined velocity signal and the detected velocity signal, a sequence of pulse signals is output to the motor 34.

The encoder 33, coaxially attached to the motor 34, detects the rotation-speed of the motor 34; namely, the rotation-speed of the rotary shutter 32, by outputting pulse signals for detecting a rotation-speed, and, further, detects the rotation-phase of the rotary shutter 32 by outputting a sequence of pulse signals for detecting a phase every time the rotary shutter 32 rotates by one rotation. The detected velocity signal output from the velocity detector T3 is fed back to the velocity comparator T6, where the detected velocity signal is added to the determined velocity signal fed from the amplifier T2. By carrying out the above feed back control, the rotation-speed is controlled. Further, the phase-signal output from the encoder 33 is fed back to the phase-comparator T7, so that the rotation-phase of the rotary shutter 32 is controlled on the basis of the difference between the detected rotation-phase and the determined shifted rotation-phase.

In this way, in the present embodiment, one rotary shutter 32 having the pair of aperture portions 32A is provided between the lamp 24 and the light guide 12. The rotary shutter 32 rotates while synchronizing with one field interval such that at least part of the irradiation interval "C" is included in the charge accumulation interval "A". Then, to maintain the proper brightness of the object image, the rotation-phase of the rotary shutter 32 is backwardly shifted by temporarily changing the rotation-speed while rotating the rotary shutter 32.

Figure 5:
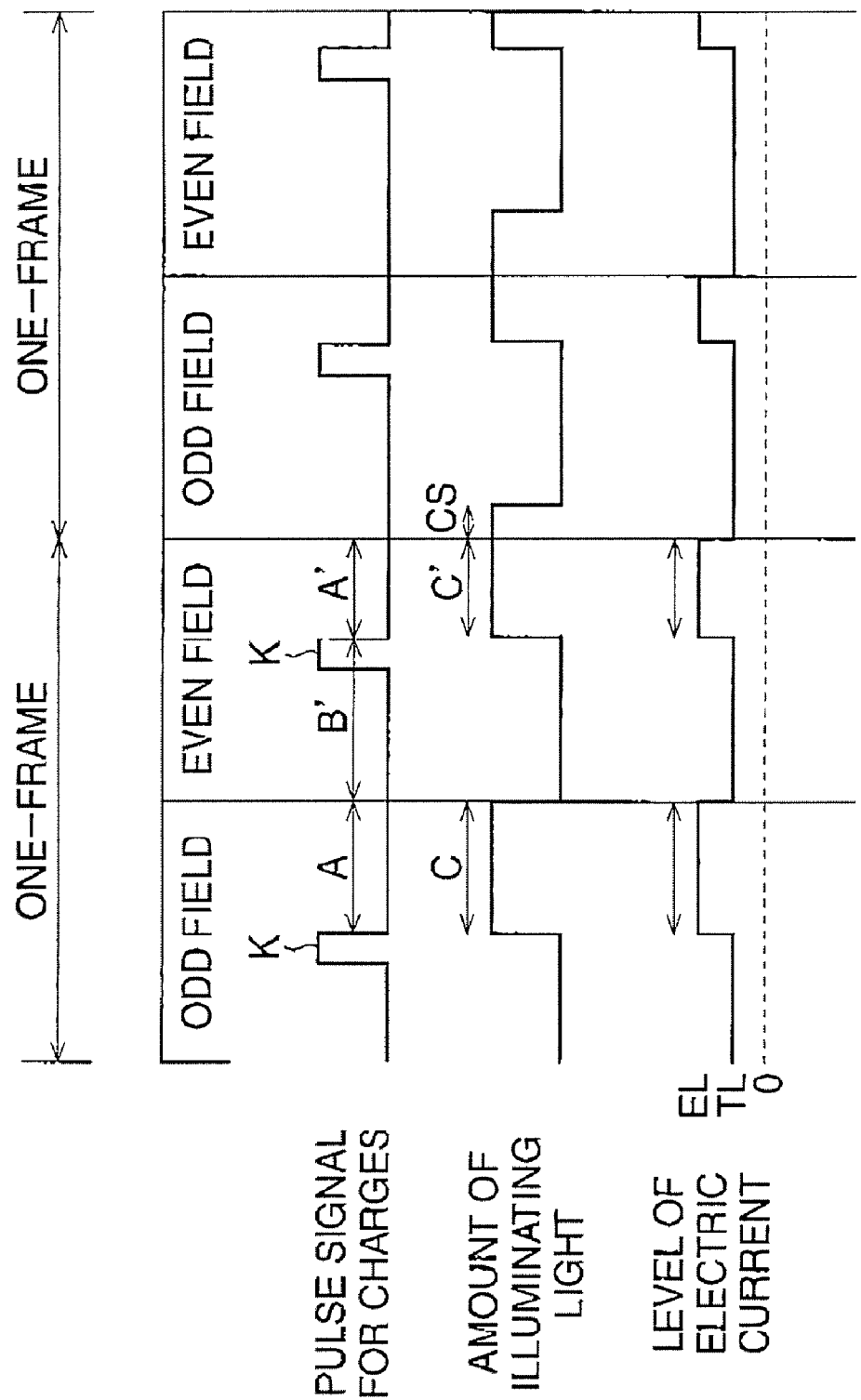
FIG. 5 is a view showing a timing chart of a brightness adjustment process according to the second embodiment.

With reference to FIG. 5, a second embodiment is explained. The second embodiment is different from the first embodiment in that the charge accumulation interval and the output power of the lamp are controlled. The other constructions are the same as those according to the first embodiment.

FIG. 5 is a view showing a timing chart of a brightness adjustment process according to the second embodiment.

Similarly to with the first embodiment, the rotation-phase is controlled such that a proper brightness is maintained. Then, when the rotation-phase is shifted, the output timing of the pulse signal "K" is adjusted in accordance with the shifted rotation-phase such that the charge accumulation interval is equal to the changed irradiation-interval "C'". In FIG. 5, the changed charge accumulation interval is designated by "A'". The output timing of the pulse signal "K" is adjusted based on a signal for changing the output timing of the pulse signal "K", which is fed from the brightness adjustment circuit 36 to the timing controller 30.

Further, the amount of electric current, supplied to the lamp 24, is controlled. Namely, the intensity of illuminating light is controlled in accordance with the varied irradiation interval. Concretely speaking, the amount of electric current is set to a normal level necessary for illuminating the object during the charge accumulation interval, whereas, during the other interval, the amount of electric current is set to a low level close to zero. Based on control signals associated with the charge accumulation interval, the system control circuit 29 control the lamp electric power supplier 22. In FIG. 5, during the charge accumulation interval "A" or "A'", the amount of electric current is set to the normal level "EL". On the other hand, the amount of electric current is set to the low level "TL" during the other interval in a one-field interval.

Note that, in the second embodiment, one of the electric current control and output control of the pulse signal "k" may be selectively carried out.

Figure 6:
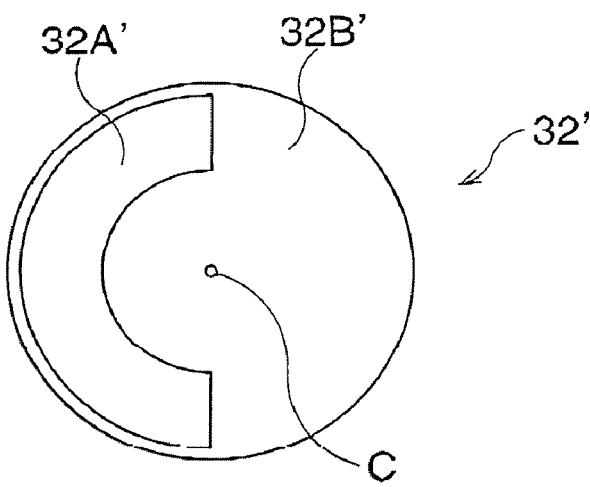
FIG. 6 is a plan view of a rotary shutter according to the third embodiment.

With reference to FIG. 6, the third embodiment is explained. The third embodiment is different from the first and second embodiments with respect to the rotary shutter. The other constructions are the same as those according to the first and second embodiments.

FIG. 6 is a plan view of a rotary shutter according to the third embodiment.

The rotary shutter 32' has an arc-shaped aperture portion 32'A, which extends circumferentially by a semi-circle. The other portion or shield portion 32'B and the aperture portion 32'A crosses the light-path alternately. The rotary shutter 32' rotates by one-rotation for one field-interval, unlike in the first embodiment.

Figure 7:
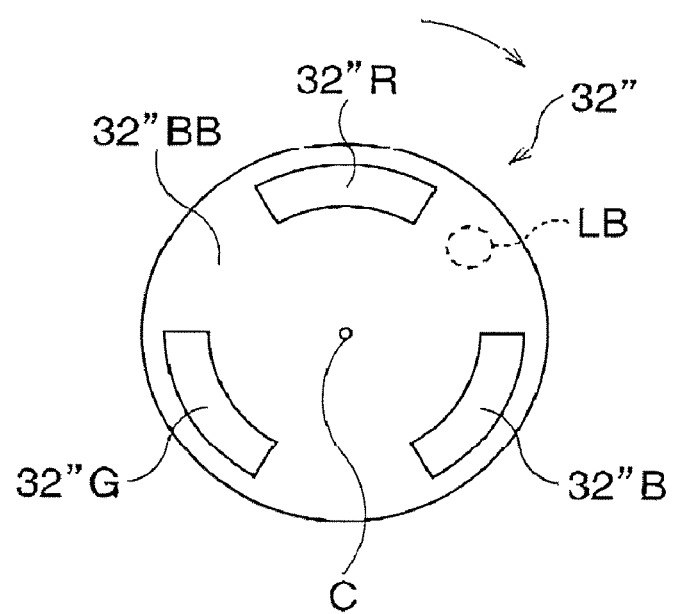
FIG. 7 is a plan view of a rotary shutter according to the fourth embodiment.

With reference to FIG. 7, the fourth embodiment is explained. The fourth embodiment is different from the first to third embodiments in that an R, G, and B sequential method is applied as the color imaging process method. Other constructions are substantially the same as those of the first to third embodiments.

FIG. 7 is a plan view of a rotary shutter according to the fourth embodiment.

The rotary shutter 32" has three aperture portions 32"R, 32"G, and 32"B, which are circumferentially formed apart from one another at constant intervals. The other portion or shield portion 32"BB separates the neighboring aperture portions. In the aperture portions 32"R, 32"G, and 32"B, a red color filter, a green color filter, and a blue color filter are provided, respectively, so that red light, green light, and blue light is irradiated on the object sequentially while the rotary shutter 32" rotates. The rotary shutter 32" rotates one rotation for one field-interval, and a clock pulse for sweeping charges are outputs three times in one field-internal in accordance with the cross-timing of each aperture portion. Based on the R, G, and B sequential method, the R, G, and B color component signals, which are generated sequentially, are synchronized with each other in an image signal processing circuit (not shown) to generate video signals. Then, similarly to with the first embodiment, the rotation-phase of the rotary shutter 32" is controlled.

The circumferential length of the aperture portion in the rotary shutter may be optionally set in accordance with the charge accumulation interval, the rotation-speed, the rotation period, etc. The rotation-phase may be forwardly shifted relative to the charge accumulation interval. Another type of motor different from a stepping motor may be applied. Another imaging process method or charge transfer method may be applied.

Finally, it will be understood by those skilled in the arts that the foregoing description is of preferred embodiments of the device, and that various changes and modifications may be made to the present invention without departing from the spirit and scope thereof.

The present disclosure relates to subject matter contained in Japanese Patent Application No. 2005-372531 (filed on Dec. 26, 2005), which is expressly incorporated herein, by reference, in its entirety.

The invention claimed is:

1. An electronic endoscope comprising:
a video-scope with an image sensor;
a light source that emits illuminating-light for illuminating an object;
an image sensor driver that outputs pulse signals for transferring charges accumulated in said image sensor in each field/frame interval, said image sensor driver outputting a pulse signal for discarding accumulated charges on the basis of a charge accumulation interval;
a luminance detector that detects a luminance of an object image on the basis of image-pixel signals read from said image sensor;
a single rotary shutter comprising a light-transmitting portion that transmits the illuminating-light, and a shield portion that blocks the illuminating light, said single rotary shutter being configured to rotate while the light-transmitting portion and the shield portion alternately cross a light-path of the illuminating-light; and
a brightness adjuster that controls said rotary shutter to change an irradiation-interval of the illuminating-light in a field/frame interval in accordance with the charge accumulation interval, said brightness adjuster shifting a rotation-phase of said rotary shutter by changing a rotation-speed of the rotary shutter on the basis of the detected luminance, so as to maintain a brightness of the object image at a proper brightness.

2. The electronic endoscope of claim 1, wherein said image sensor driver adjusts the charge accumulation interval to the irradiation interval in one field/frame interval in accordance with the shifted rotation-phase.

3. The electronic endoscope of claim 1, further comprising a light source controller that is capable of selectively setting an intensity level of illuminating light to one of a normal level required for illuminating an object and a low level adjacent to zero level, said light source controller setting the normal level for the irradiation interval, and setting the low level for an other interval.

4. The electronic endoscope of claim 1, wherein said light-transmitting portion comprises a pair of aperture portions, said pair of aperture portion being opposite each other and each extending circumferentially by a quarter-circle.

5. The electronic endoscope of claim 1, wherein said light-transmitting portion comprises an aperture portion, said aperture portion extending circumferentially by a semi-circle.

6. The electronic endoscope of claim 1, wherein said light-transmitting portion comprises R, G, and B color filters extending circumferentially and spaced from one another at regular intervals.

7. The electronic endoscope according to claim 1, wherein said brightness adjuster changes an illumination time from a start to an end of the field/frame interval by shifting a rotation phase of said rotary shutter.

8. An apparatus for adjusting a brightness of an object image in an electronic endoscope, comprising:
a luminance detector that detects a luminance level of an object image on the basis of image-pixel signals that are read from an image sensor of a video-scope successively;
a single rotary shutter comprising a light-transmitting portion and a shield portion, said single rotary shutter being configured to rotate while the light-transmitting portion and the shield portion alternately cross a light-path of the illuminating-light; and
a brightness adjuster that controls said rotary shutter to adjust an irradiation interval of the illuminating light in a field/frame interval in accordance with a charge accumulation interval of said image sensor, said brightness adjuster changing an overlapping interval of the irradiation interval and the charge accumulation interval by shifting a rotation-phase of said rotary shutter on the basis of the detected luminance level, so as to maintain a brightness of the object image at a proper brightness.

9. The apparatus for adjusting a brightness according to claim 8, further comprising a light source controller that is capable of selectively setting an intensity level of illuminating light to one of a normal level required for illuminating an object and a low-level, adjacent to zero level, said light source controller setting the normal level for the irradiation interval, and setting the low-level for another interval.

10. The apparatus for adjusting a brightness according to claim 8, wherein said light transmitting portion comprises a pair of aperture portions, said pair of aperture portions being opposite each other and each extending circumferentially for 90°.

11. The apparatus for adjusting a brightness according to claim 8, wherein said light transmitting portion comprises an aperture portion, said aperture portion extending circumferentially for 180°.

12. The apparatus for adjusting a brightness according to claim 8, wherein said light transmitting portion comprises R, G and B color filters extending circumferentially and spaced from one another at regular intervals.

13. The apparatus for adjusting a brightness according to claim 8, wherein said brightness adjuster changes an illumination time from a start to an end of the field/frame interval by shifting a rotation phase of said rotary shutter.

14. The apparatus for adjusting a brightness according to claim 8, wherein said brightness adjuster decreases the rotation speed of said rotary shutter in response to the detected luminance level exceeding a reference luminance level.

15. A method for adjusting a brightness of an object image in an electronic endoscope, comprising:
  detecting a luminance level of an object image on the basis of image-pixel signals that are read from an image sensor of a video-scope successively;
  rotating a single rotary shutter that comprises a light-transmitting portion and a shield portion, such that the single rotary shutter rotates while the light-transmitting portion and the shield portion alternately cross a light-path of the illuminating-light; and
  controlling the rotary shutter to adjust an irradiation interval of the illuminating light in a field/frame interval in accordance with a charge accumulation interval of the image sensor, the controlling comprising changing an overlapping interval of the irradiation interval and the charge accumulation interval by shifting a rotation-phase of the rotary shutter on the basis of the detected luminance level, so as to maintain a brightness of the object image at a proper brightness.

16. The method for adjusting a brightness according to claim 15, further comprising selectively setting an intensity level of illuminating light to one of a normal level required for illuminating an object and a low-level, adjacent to zero level, and setting the normal level for the irradiation interval and setting the low-level for another interval.

17. The method for adjusting a brightness according to claim 15, wherein the light transmitting portion comprises a pair of aperture portions, the pair of aperture portions being opposite each other and each extending circumferentially for 90°.

18. The method for adjusting a brightness according to claim 15, wherein the light transmitting portion comprises an aperture portion, the aperture portion extending circumferentially for 180°.

19. The method for adjusting a brightness according to claim 15, wherein the light transmitting portion comprises R, G, and B color filters extending circumferentially and spaced from one another at regular intervals.

20. The method for adjusting a brightness according to claim 15, wherein the controlling comprises changing an illumination time from a start to an end of the field/frame interval by shifting a rotation phase of the rotary shutter.

* * * * *